(12) United States Patent
Petricoin, III et al.

(10) Patent No.: US 11,574,718 B2
(45) Date of Patent: Feb. 7, 2023

(54) OUTCOME DRIVEN PERSONA-TYPING FOR PRECISION ONCOLOGY

(71) Applicant: PERTHERA, INC., McLean, VA (US)

(72) Inventors: Emanuel Frank Petricoin, III, Gainesville, VA (US); Robert Joseph Bender, Rockville, MD (US)

(73) Assignee: PERTHERA, INC., McLean, VA (US)

( * ) Notice: Subject to any disclaimer, the term of this patent is extended or adjusted under 35 U.S.C. 154(b) by 80 days.

(21) Appl. No.: 16/428,500

(22) Filed: May 31, 2019

(65) Prior Publication Data

US 2019/0371443 A1   Dec. 5, 2019

Related U.S. Application Data

(60) Provisional application No. 62/678,896, filed on May 31, 2018.

(51) Int. Cl.
*G16H 20/10* (2018.01)
*G16H 10/60* (2018.01)
*G16H 50/70* (2018.01)

(52) U.S. Cl.
CPC ............. *G16H 20/10* (2018.01); *G16H 10/60* (2018.01); *G16H 50/70* (2018.01)

(58) Field of Classification Search
CPC ......... G16H 50/70; G16H 20/10; G16H 10/60
See application file for complete search history.

(56) References Cited

U.S. PATENT DOCUMENTS

| | | | |
|---|---|---|---|
| 2003/0004906 A1* | 1/2003 | Lapointe | G16H 50/20 706/924 |
| 2008/0033899 A1* | 2/2008 | Barnhill | G06Q 10/0637 706/48 |
| 2008/0261820 A1 | 10/2008 | Iyengar et al. | |
| 2009/0132460 A1* | 5/2009 | Alemi | G16H 10/60 706/52 |
| 2014/0279746 A1* | 9/2014 | De Bruin | G16H 10/60 706/46 |
| 2015/0019239 A1 | 1/2015 | Ebadollahi et al. | |
| 2015/0363559 A1* | 12/2015 | Jackson | G16B 50/00 705/2 |
| 2016/0224760 A1* | 8/2016 | Petak | G16H 50/70 |
| 2016/0232309 A1 | 8/2016 | Yoon et al. | |
| 2018/0039731 A1 | 2/2018 | Szeto | |
| 2018/0357372 A1* | 12/2018 | Bagaev | G16B 45/00 |
| 2019/0057182 A1* | 2/2019 | Klement | G06N 5/02 |
| 2019/0295702 A1* | 9/2019 | Das | G16H 20/10 |

(Continued)

*Primary Examiner* — Robert W Morgan
*Assistant Examiner* — Chance L Smith
(74) *Attorney, Agent, or Firm* — Troutman Pepper Hamilton Sanders LLP

(57) ABSTRACT

A method and system are disclosed for performing supervised outcome-driven persona-typing, including receiving a first data set having patient specific data, treatment data, and outcome data for each of a plurality of first patients. Once received, the plurality of first patients are grouped based on the first data set, and a persona for each of patient groups is generated. A second data set may then be received for a second patient including second patient specific data. A comparison is then carried out on the second data set to identify an existing persona, and then associate the second patient with the identified persona. Based on each of the above steps, a patient care plan is then created.

17 Claims, 6 Drawing Sheets

(56) References Cited

U.S. PATENT DOCUMENTS

2019/0341153 A1* 11/2019 Ng .................. G16H 50/50
2020/0185063 A1*  6/2020 Narain ............. G16B 25/00
2020/0411199 A1* 12/2020 Shrager ........... G16H 15/00

* cited by examiner

OUTCOME DRIVEN PERSONA-TYPING FOR PRECISION ONCOLOGY

CROSS-REFERENCE TO RELATED APPLICATION

This application claims priority to and the full benefit of U.S. Provisional Patent Application No. 62/678,896, filed May 31, 2018 and entitled OUTCOME DRIVEN PERSONA-TYPING FOR PRECISION ONCOLOGY. The entirety of U.S. Provisional Patent Application No. 62/678,896 is incorporated by reference herein.

TECHNICAL FIELD

The present disclosure relates to processes and techniques for recommending treatment for a patient using a variable weighting-based scoring algorithm. More specifically, the present disclosure relates to a scoring algorithm where certain patient and molecular data are analyzed to develop a patient care plan.

BACKGROUND

Genetic information from patients allows the possibility of precision oncology and treatments for patients that are individualized. However, genetic information alone may not be sufficient. For example, a genomic profiling study reveals actionable mutations affecting signaling pathways, but in spite of these mutations, targeted inhibitors of these pathways may have low success rates. A possible reason for these failures is that single-gene biomarkers may fail to account for crosstalk within and between dysregulated pathways. Multi-omic profiling based on multiple biomarkers, genetic and molecular information and patient history can help make better molecular recommendations for treatment.

There has been an explosion in the number of drugs being developed specifically for cancer—nearly 1,000 separate drugs are currently at various stages of being tested for safety and efficacy. This growth in new drugs is associated with an evolution of precision medicine. However, it is unlikely that an oncologist can keep up with all of the science and progress established though these clinical trials or all of the published literature on disease treatments.

Accordingly, there remains a need for a system and process of patient evaluation that creates a comprehensive patient care plan.

SUMMARY

A method for determining a recommendation for drug treatment is described herein. In certain implementations, the method includes determining drug scores based upon network-based distances for one or more target drug nodes, modeling one or more outputs based upon input data, wherein the input data comprises at least a portion of the drug scores, selecting an algorithmic output from the one or more modeling outputs based upon at least one performance criteria, determining whether the selected algorithmic output of the modeling satisfies a threshold, and, if the selected algorithmic output satisfies the threshold, generating the recommendation for drug treatment.

A system for determining a recommendation for drug treatment is also described herein. In certain implementations, the system includes a processing device and a computer readable medium operably connected to the processing device. The computer readable medium can include programming instructions that, when executed, cause the processing device to determine drug scores based upon network-based distances for one or more target drug nodes, model one or more outputs based upon input data, wherein the input data comprises at least a portion of the drug scores, select an algorithmic output from the one or more modeling outputs based upon at least one performance criteria, determine whether the selected algorithmic output of the modeling satisfies a threshold, and, if the selected algorithmic output satisfies the threshold, generate the recommendation for drug treatment.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION

Figure 1:
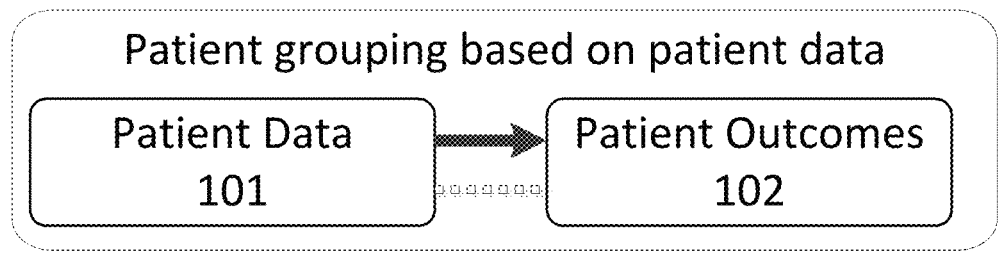
FIG. 1 depicts an illustrative sample process for grouping patients in accordance with an embodiment.
Figure 1:
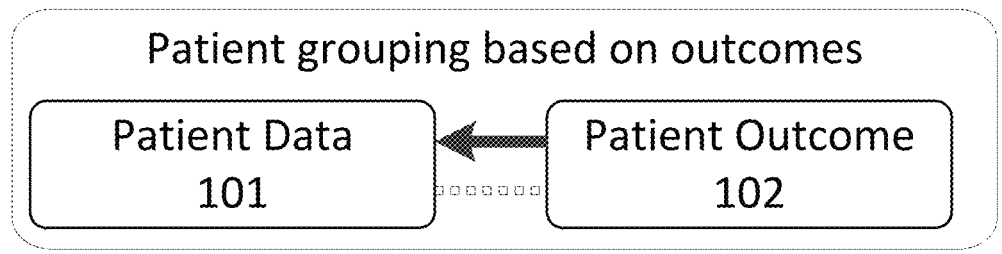
Figure 1:
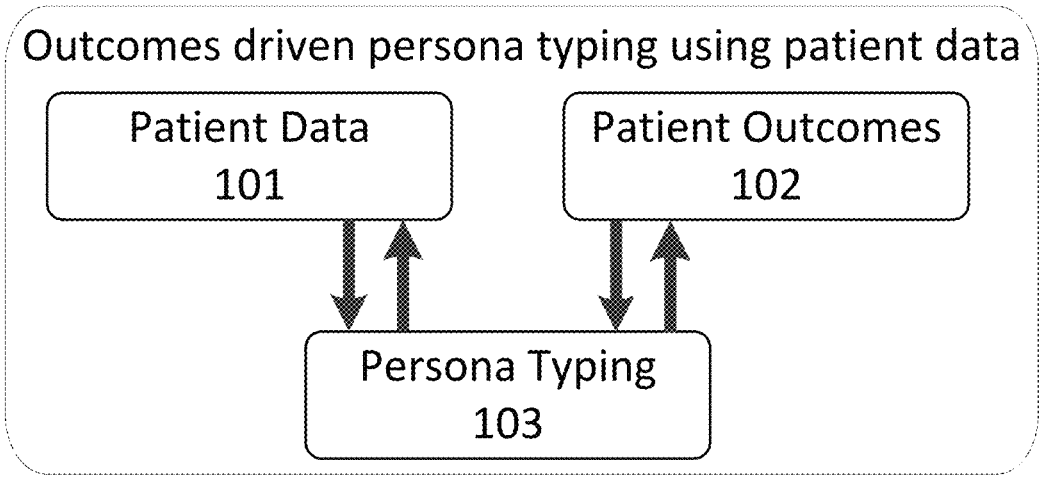

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

As used herein, the term "patient" may refer to an individual or to any subject/sample (e.g., patient-derived cells, organoids, xenografts, avatars, snapshot(s) of patient data in time and/or space, or other experimental/preclinical/clinical representations/models, either in vivo, in vitro, in silico, in animals, in humans, etc.

The present disclosure is directed to a process for deriving outcome driven persona-types for precision oncology. In some embodiments, two types of input data may be used: (1) molecular data generated from a patient tumor specimen;

and (2) a biomolecular interaction network. For example, the molecular data can be any combination of multi-omic data. Frequent data types, can include genomic, transcriptomic, proteomic, and phosphoproteomic, but the processes and techniques as described herein are flexible and can accept other data types such as epigenetic and other post-translational modifications as well. Typical applications of the invention will utilize data from commercial laboratories, but research/investigational use data can also be used as input.

The techniques and processes as described herein can also make use of a biomolecular interaction network containing representations of various types of reactions that occur within signaling pathways of biological systems. In certain implementations, publicly available network databases, such as Reactome and the National Cancer Institute Pathway Interaction Database, can form the basis of this network. The basic network can be expanded so that each distinct protein includes nodes for DNA, RNA, protein, and all activity states of the protein (if applicable). For example, the public network databases generally include the HER2/ERBB2 protein and its active phosphorylated form. The network used in the present disclosure could be expanded to include the DNA and mRNA encoding HER2 as well. In certain implementations as described herein, the expanded network used in the weighting algorithm can be a structured as a graph with directed edges.

Thus, as discussed herein, various embodiments represent improvements to computational methodologies and algorithms to match and rank therapy options to patients previous treatment history, clinical data, and multi-omic molecular data (tumor profiling). In a further embodiment, the system also collects outcomes data to produce a structured database that contains dozens to hundreds of data fields of binary (e.g., gender) and high dimensional multivariate quantitative data (e.g., levels of protein expression). Thus, various embodiments discussed herein may incorporate experience-gaining (e.g., artificial intelligence) based approaches to its treatment matching algorithms The ability to generate "personas" based on the aggregate of all structured data in N-dimensional space could be of great value in identifying phenotypic characteristics shared by patients with common features that is used for treatment selection optimization.

Once these features, or principal components have been identified that specify each persona, then an incoming patient, that was not part of the population of data that was used to build the outcome-driven "personas" can be fit into the "persona" that the patient most closely resembles, and then the treatment strategy that underpinned that persona's outcome would represent a potential best-fit for that patient. Through iterative experience gaining of the entire system, the outcome data expands with more and more patient experiences, and the outcome driven personas can be further refined through cluster expansion, or collapse to become optimized.

Accordingly, as discussed, various embodiments are presented herein related to computational methodologies and algorithms, which match and/or rank potential therapy options based on a number of factors (e.g., the patient's previous treatment history, clinical data, and multi-omic molecular data (i.e., tumor profiling)). The system may also collect outcome data for one or more patients in order to produce a structured database that contains data fields of binary (e.g., gender) and high dimensional multivariate quantitative data (e.g., levels of protein expression). In a further embodiment, the system may learn or gain experience from performing processes (e.g., artificial intelligence), which may be based on one or more treatment matching algorithms. In other words, the system as disclosed herein may have the ability to generate one or more "personas" based on the aggregate of all of the structured data in N-dimensional space.

It should be understood that persona or persona type, as used herein, are not necessarily confined to a single patient type. The utility of mixtures of patient types (e.g., patient primary tumors and matched patient-derived xenograft tumors) may embody statistical approaches that are paired in nature (e.g., the p-value from a paired T-test, a ratio of features measured in both sample types). Furthermore, the definition of a "patient" may also extend longitudinally when analyzing data collected at multiple time points (e.g., time-course data, pre/post-treatment data, etc.) in the context of persona typing.

The system may, in some embodiments, identify one or more phenotypic characteristics that are shared by patients with common features (e.g., features used for treatment selection optimization, such as those discussed herein). In one embodiment, the clinical outcome (i.e., the response to a given therapy, how well a patient did on a drug) may be the most important determination to use as a selective pressure filter when determining commonality in one or more "personas." These may be measured using various metrics, such as, for example, progression-free survival, overall survival, time to progression, relapse-free survival, metastasis-free survival, etc.

Thus, with an adequately sized database of a population of patient's data, an embodiment may select one or more outcome driven "personas" from a population that share common outcome determinants, for example, by using a forced supervised clustering based on outcome data, as a continuous variable or label (e.g., dead or alive). The system may then look in N-dimensional space of the total population for the features that principally define those patients with common outcome "personas." In some embodiments, the features may be selected from the entirety, or a portion, of select elements of the data collected (e.g., gender, age, race, clinical diagnostic variables, tumor molecular data, treatment history, etc.).

In a further embodiment, each feature may be individually weighted mathematically and then used by the system to determine which of all of the variables collected best describes each cluster and/or discriminates them from each other. Once the system has identified the features or principal components that specify each persona, an incoming patient that was not part of the population of data (i.e., original data set) that was used to build the outcome-driven personas may be evaluated to determine if they fit into one of the generated personas. Thus, the patient would be associated with an existing persona that they most closely resemble. Based on the persona association, the system can identify the treatment strategy that underpinned the associated persona, which would represent a potential best-fit for that patient.

In some embodiments, an iterative system is utilized that gains experience (i.e., acquires more data, improvises persona grouping and alignment etc.) from the entire system, the outcome data expanding with more and more patient experiences. The outcome driven personas can be further refined and cluster expansion or collapse can become optimized.

In another embodiment, the system may collect outcome data to produce a structured database that contains dozens to hundreds of data fields of qualitative and high dimensional multivariate quantitative data. In a further embodiment, the system may utilize machine-learning, neural network, and/ or an artificial intelligence to carry out the matching algorithms and generate one or more personas. Through the use of machine-learning, a neural network, and/or artificial intelligence, the system may generate personas based on the aggregate of all structured data in N-dimensional space. The generated personas may then be used to identify phenotypic characteristics, which are shared by patients with common features (i.e., features used for treatment selection optimization).

As discussed, a patient's clinical outcome response to a given therapy is a critical determination factor that the system can use as a selective pressure filter to determine one or more commonalities. Non-limiting examples of commonalities may include, but are not limited to: a measure of in-progression free survival, a derivative of in-progression free survival, overall survival, time to progression, relapse free survival, metastasis free survival, tumor shrinkage, tolerability, complete response rate, partial response rate, overall response rate, disease control rate, etc.

In a further embodiment, supervised or semi-supervised clustering algorithms and other data science modeling approaches may be applied to understand the relationships between patient input data and patient outcome data. Moreover, the system may also perform regression analysis, machine learning, and/or artificial intelligence on quantitative and qualitative patient data to identify outcome driven "personas" from within a population ("cohort" often defined by cancer type and/or other clinical attributes that is being considered for stratification into one or more "personas") that share common outcome determinants In some embodiments, the system may look in N-dimensional space of the total population for the features that principally define those patients with common outcome "personas."

Stated differently, a universe that contains the outcomes-driven personas (i.e., persona-verse) is essentially created to group patients into the various personas based on the identified features. In an embodiment, these features may be selected from the entirety or a subset) of the data collected (e.g., gender, age, race, clinical diagnostic variables, tumor molecular data, treatment history, comorbidities, smoking history, etc.), all of which can be mathematically interpreted (e.g., equally weighted, manually weighted, z-score normalized, etc.).

In a further embodiment, the system may use the weighted features to determine which, of all of the variables collected, best describes each cluster, and discriminates them from each other. Once the features or derived features (e.g., principal components) that specify (i.e., define) each persona have been identified, an incoming patient, who was not part of the original population of data, can be fit into a "persona" that most closely resembles the patient. Based on the selected persona, the system may, in some embodiments, determine a treatment strategy based on the strategy that underpinned that persona.

For example, in one embodiment, the system collected multiplexed data of approximately 500 data fields including clinical, epidemiologic, multi-omic molecular, etc. The multiplexed data had a large number (~700) of pancreatic cancer patients along with the chart-abstracted outcomes data. In one embodiment, the system may create a series of 10 outcome-driven personas, based on a forced binning of the continuous variable progression-free survival data from these patients that spanned the collected PFS data.

In another embodiment, the system may use a non-parametric based ANOVA analysis to evaluate which of the ~500 data features (e.g., continuous and/or dichotomized) best discriminates each of the outcome driven personas. In this embodiment, the identification of specific molecular features, such as increased levels of PD-1 protein expression, increased incidence of BRCA2 genomic alterations, increased frequency to prior treatment with gemcitabine, etc., defined the outcome persona-type that had the best overall survival. Accordingly, as the population of patients, data, and outcomes expands, the personas will automatically update their scope and factors.

In another embodiment, the system may analyze patient data from a cohort of 1047 patients with advanced pancreatic cancer. Non-limiting examples of patient data may include: clinical data elements, captured age group at diagnosis, gender, race, ethnicity, nationality, menopausal status, diabetes type (e.g., none, type 1, type 2), age at onset of diabetes, smoking status (e.g., current smoker, former smoker, never smoked), smoking quantitative history (e.g., in pack years), pancreatic cancer subtype (e.g., adenocarcinoma, adenosquamous carcinoma, acinar cell carcinoma, pancreatoblastoma, etc.), tumor stage at diagnosis (e.g., stage IIB, stage IV, T2N1Mx, etc.), prior history of neoadjuvant/adjuvant treatment and their relatedness to therapies given in the advanced setting.

In another embodiment, molecular data elements may include, but are not limited to, genomic (e.g., BRAF fusion, BRCA2 germline mutation, CDK4/CDK6 amplification with a copy number ratio of at least 2), transcriptomic (e g , "immune desert" signature based on multigene analysis), proteomic (e.g., HER2 intensity score as 3 or higher by IHC, PD-L1 combined propensity score by IHC), phosphoproteomic (e.g., phospho-AKT positivity on tumor cells by IHC and/or RPPA), metabolomic (e.g., blood glucose; ammonia in urine, etc.), and radiotracers (e.g., FDG uptake, dotatate scans, etc.).

In this embodiment, the system may perform a pathway-level actionability analysis that can summarize molecular testing results into numeric vectors representing biomarker-based treatment implications spanning various therapeutic interventions (e.g., individual chemotherapies, immunotherapies, targeted therapies, radiation therapies, surgical interventions, multi-agent cocktails, etc.). As a result of this preprocessing step, the size of the numeric matrix used an input for classifying one or more patients into a persona type could be reduced from 1047×1078 to 34×1078. Accordingly, the system allows for an improvement not just in precision oncology, but also as it relates to computer improvements via software.

The following non-limiting example is presented herein to further demonstrate the advantages of outcome-driven persona typing. In an embodiment, the system may analyze a subset of 454 patients, for which treatment outcomes are available for FOLFIRNOX or FOLFOX (i.e., implemented as a standard of care, with other agents on a clinical trial, or off label).

In other embodiments, the persona typing method can also utilize patient data including but not limited to censored outcomes data, binarized outcomes data, treatment duration data, partial responses, complete responses, disease controls, or cohort-level derivatives of these types of values (e.g., overall response rates). In some embodiments, multiple outcome data types may be used when exploring potential methodological refinements, when implementing classification methods trained simultaneously, or sequentially, on multiple outputs, or when an independent-validation outcomes dataset uses a urrogate endpoint (e.g., real-world progression-free survival) that is different from the cross-validation dataset (e.g., overall survival).

Figure 2:
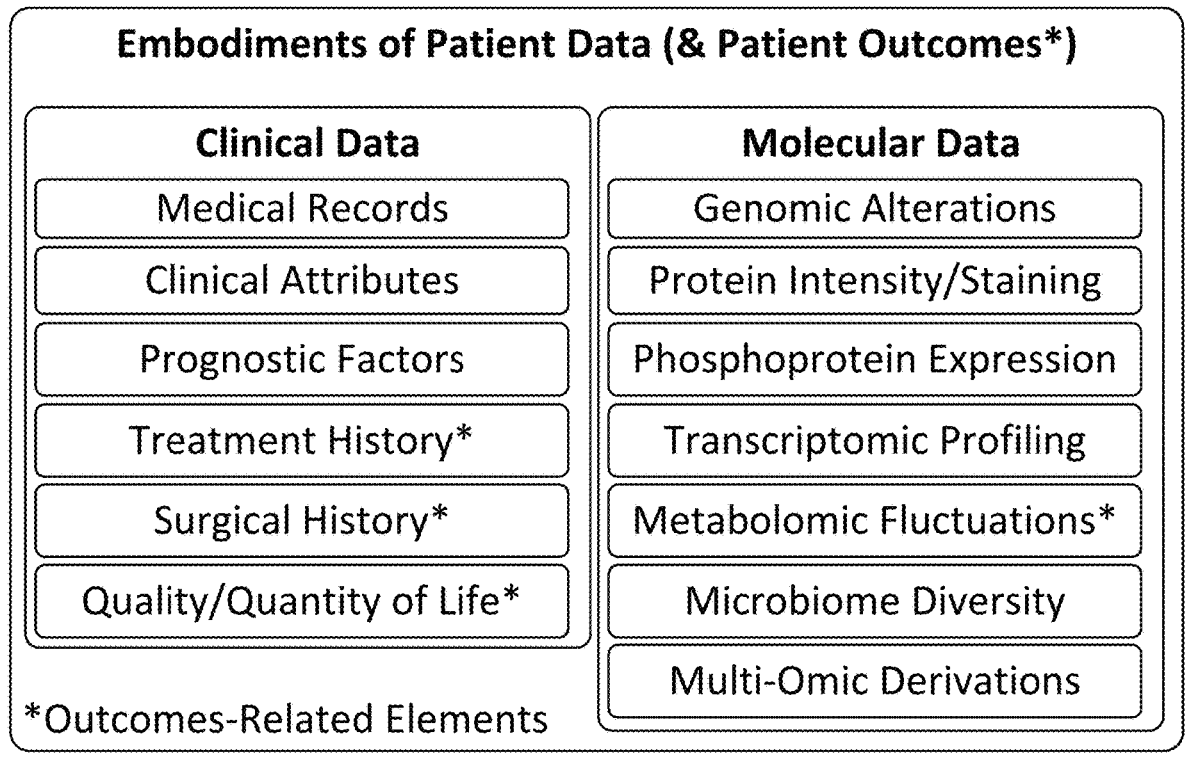
FIG. 2 depicts example embodiments of patient data and patient outcomes in accordance with an embodiment.

Referring now to FIG. 1, an illustrative example of an embodiment is shown. As discussed herein, outcome-driven persona-typing can leverage patient data 101, patient outcomes 102, and/or dynamically-refined "persona typing" methods 103. In some embodiments, patient data 101 may represent any clinical and/or molecular data (e.g., structured or unstructured) that could be considered appropriate for classifying one or more patients into one or more persona types 103. As discussed herein, many features of the patient data 101 may be useful as a response variable and/or as a predictor variable. In an additional embodiment, the system may perform mathematical and/or statistical analyses of outcome-driven persona typing, which may require analyzing at least one of the patient's quality of life (e.g., patient-reported, provider-reported, and/or EMR-reported), duration of life (e.g., overall survival from time of advanced diagnosis), and/or time on therapy (e.g., months on treatment without disease progression or death) across persona types. Additional examples of clinical data (e.g., medical records, clinical attributes, prognostic factors, treatment history, surgical history, quality of life, quantity of life, etc.) and molecular data (e.g., genomic alterations, protein intensity, protein staining, phosphoprotein expression, transcriptomic profiling, metabolomic fluctuations, microbiome diversity, multi-omic derivations, etc.) are shown in FIG. 2. In addition, FIG. 2 identifies which of the data sets may be outcomes-related elements.

Figure 3:
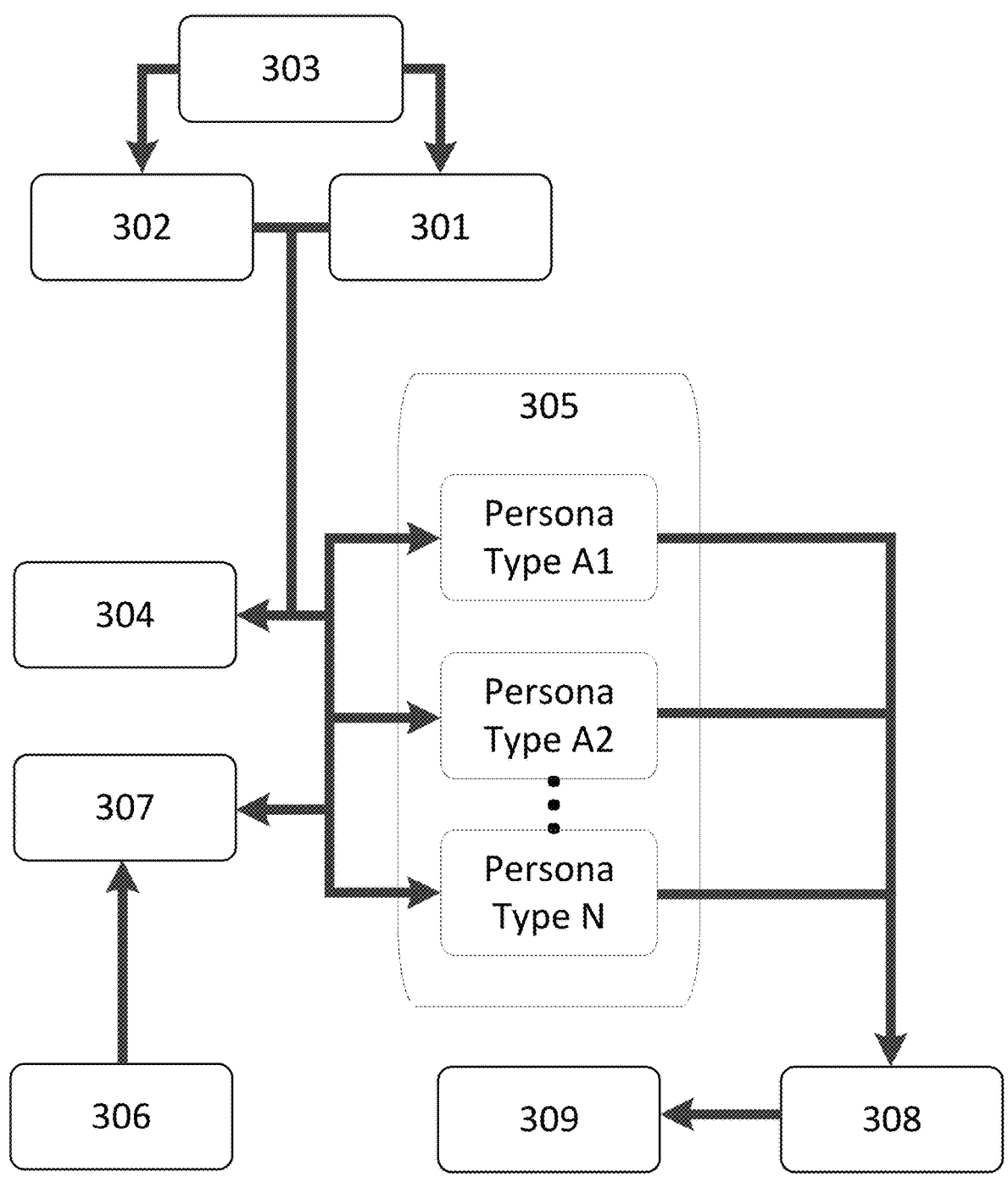
FIG. 3 depicts an example process flow in accordance with an embodiment.

Referring now to FIG. 3, an illustrative flow chart of an embodiment is shown. As discussed herein, an embodiment may receive patient data 301 and patient outcome data 302. In some embodiments, the system may apply cohort definitions 303 to the patient data 301 and/or the patient outcomes 302. The received data (i.e., 301 and 302) as well as the cohort definitions 303 are sent to the training/validating/iterating classification method 304 as well as the persona-verse 305. As shown, and described herein, the persona-verse 305 may comprise one or more persona types (e.g., persona type A1, A2, A3. . . N). Thus, in some embodiments, the classification module 304 analyzes all the received and known data to create and/or identify one or more persona types.

Once a persona has been identified as a best fit, the system may identify one or more persona inferences 308. In a further embodiment, the system may receive one or more new patient information 306 (e.g., new patient data and new patient outcomes, etc.). The new patient information 306 may then be passed to the application/assignment method 307. Similar to classification method 304, classification method 307 may then pass the analyzed data into the persona-verse 305 in order to assign the new patient to one or more existing personas and/or create one or more new personas.

It should be understood that the classification modules 304 and 307 may be any known or future sorting/grouping method, such as, for example, at least one of: an expert system, heuristic rules, a decision tree, a Bayesian network, linear and/or non-linear models, logistic regression, cox regression, natural language processing, image processing, support vector machine, machine learning, deep learning, neural network learning, and artificial intelligence.

In some embodiments, when new patient data 301 and patient outcomes 302 are received by the system, and the classification module 307 analyzes the data, various persona type inferences may be drawn, such as, for example, the new patient may: be associated with decreased sensitivity to anti-PD-1 antibodies, influence clinical decision-making for medical oncologists, influence access to a treatment (e.g., by a regulatory agency), influence access to a clinical trial (e.g., based on eligibility or logistics), influence authorization/pre-authorization (e.g., by an insurer), influence the Classification Method in future iterations/versions, have no significant inferential associations, prompt a provider to change treatment due to increased risk of toxicity, and after prior assignment (e.g., when new data is available) may be inferential. It should be understood that the above list is for explanatory purposes only and is not intended to limit further persona inferences that may be made by the system.

Figure 4:
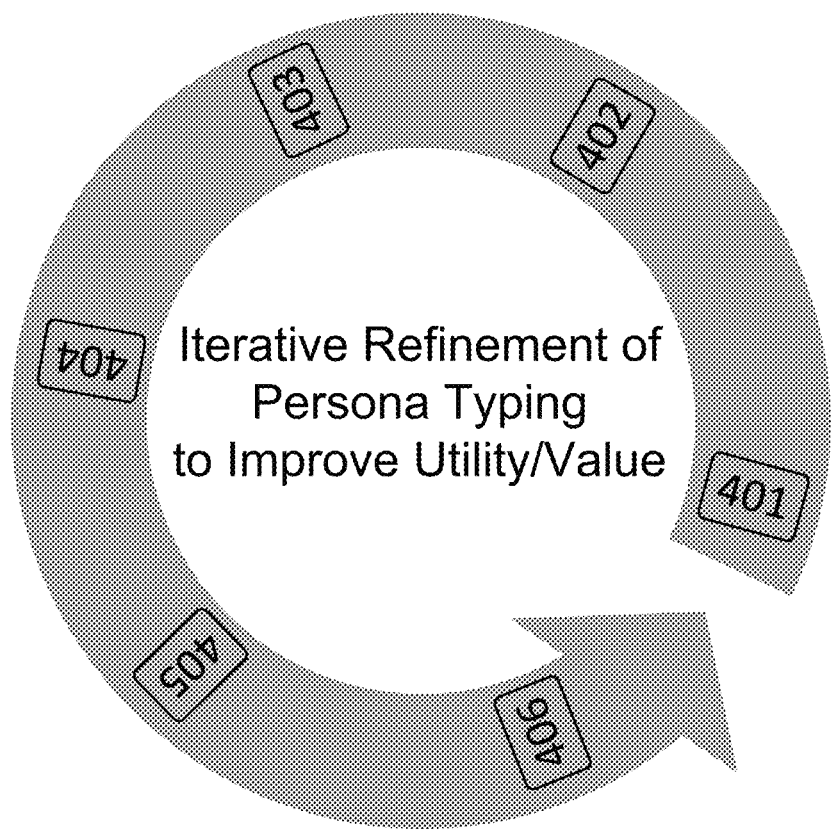
FIG. 4 depicts an illustrative example of the iterative refinement process in accordance with an embodiment.

Referring to FIG. 4, an illustrative example of how the system utilizes metrics for utility and value according to an embodiment is disclosed. As discussed herein, in some embodiments, the system performs an iterative refinement of the persona typing to improve the utility, functionality, and value of the system. As shown, the system begins the improvement iterations with the clinical benefit of persona typing use 401 (e.g., hazard ratios, RCT endpoints, etc.). In a further embodiment, the cost effectiveness of persona typing use may be evaluated 402 (e.g., ICER, CDS efficiency, etc.). Next, a quantitative predictive performance evaluation 403 may be performed (e.g., sensitivity, specificity, TPR, FPR, AUC, MCC, etc.). This may allow the system to become more robust with regard to new patient data/outcomes 404. Moreover, in some embodiments, the scalability and feasibility of the persona typing is reviewed and potentially adjusted 405. Finally, in some embodiments, the system may have a qualitative assessment feature 406 (e.g., to receive and review user feedback, expert opinions, consensus models, and interpretability).

In another embodiment, the system as a whole may be scalable in nature. More specifically, the system may scalably enable the iterative-refinement and continual-optimization of any persona-typing methods in ways that are manual, semi-automated (e.g., by algorithmically prioritizing features for manual selection/elimination/aggregation) and/or fully automated (e.g., assuming sufficient patient data/outcomes are considered reliable enough to decouple manual effort from system improvements.)

Figure 5:
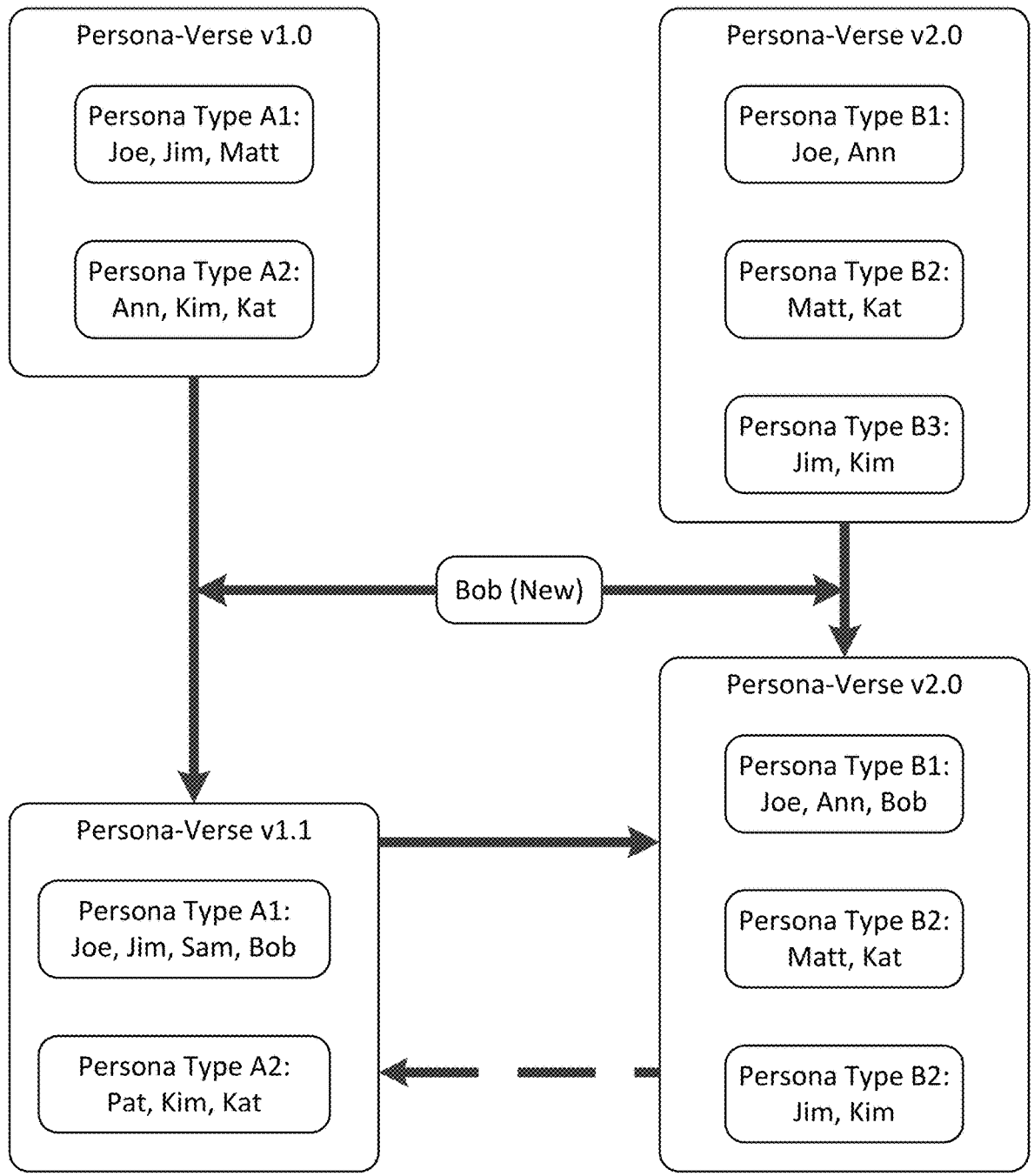
FIG. 5 depicts an illustrative example where a new patient is introduced to the system in accordance with an embodiment.

Referring now to FIG. 5, an example embodiment is shown, in which a new patient (i.e., Bob) is introduced to the system. As shown, in the persona-verse 1.0, the individuals are grouped into two persona types, based on their biological sex. Specifically, Joe, Jim, and Matt are categorized as males, while Ann, Kim, and Kat are categorized as females. Thus, in persona-verse 1.1, Bob has been included in persona type A1. Alternatively, in persona-verse 2.0, persona type B3 is grouped based on the last letter of the patient's name ending in M, while persona type B2 is grouped based on the last letter of the patient's name ending in T, and finally persona type B1 is grouped as a catch all for those not assigned to a restricted persona type. It should be understood that these examples are extremely rudimentary, and in fact may have no benefit or bearing on outcome driven persona-typing for precision oncology.

Generally, patient outcome datasets related to treatment history are relatively sparse when compared to clinical data and molecular data elements. In some embodiments, pre-processing the patient data may reduce the risk of overfitting dense clinical/molecular datasets (e.g., those with 100-10000+features) into personas that only have sparse outcomes. Accordingly, as discussed herein, various machine learning, neural networks, and artificial intelligence algorithms can be used to assist with feature elimination, prioritization, aggregation (e.g., principal component analysis) which may or may not leverage bootstrapping approaches, cross-validation with one or more sets of training data, cross-training validation data, and independent validation data (possibly prospective).

Thus, in an embodiment, the system may preprocess the patient data and standardized it into a quantitative matrix format that is considered appropriate for applying both supervised and/or unsupervised machine learning algorithms, artificial intelligence, and neural networks. In an additional or alternative embodiment, a semi-supervised approach may be utilized to define persona types. In this embodiment, the system performs multiple unsupervised methodologies (e.g., K-means clustering, statistical analysis, etc.) with varying parameters (e.g., k=1,2,3, . . . , n) followed by manual selection of top performing methodologies.

In another embodiment, the system may analyze a dataset of patients with pancreatic cancer, who had molecular testing of their tumors completed by a commercial CLIA/CAP laboratory. Thus, in this embodiment, the patient data was aggregated from multiple cancer centers through a nationwide program. In a further embodiment, the criteria for analyzing this cohort may have indicated the presence of a pathogenic or likely pathogenic BRAF, ARAF, or CRAF mutation. In this example embodiment, the BRAF mutation pathogenicity was classified independently by the testing laboratory for each patient on a case-by-case basis and was also assessed by multiple researchers who leveraged public and private data/information.

In another example embodiment, semi-supervised clustering was carried out on the molecular data and the clinical data which produced four (4) classes of BRAF-mutant pancreatic cancers which were named as follows: BRAF V600 (characterized by mutations that are thought to be biologically/functionally similar to BRAF p.V600E, the most prevalent variant in melanoma), BRAF Fusions (characterized by genomic fusion/rearrangement/translocation events such as the SND1-BRAF fusion), BRAF non-V600 (characterized by insertion/deletions such as BRAF p.N486_P490del and select missense mutations), and, lastly, BRAF "Other" (characterized by "Class 3" mutations and/or the presence of genomic mutation in a secondary oncogenic driver such as a KRAS p.G12D mutation or an NTRK3 activating fusion). It should be noted that that "Class 1" BRAF alterations are similarly classified to the BRAF V600 Persona Type, whereas "Class 2" mutations may encompasses both the BRAF Fusions and the BRAF non-V600 Persona Types.

To further demonstrate the utility of an outcomes-driven approach, comparative progression-free survival data was analyzed across persona types for molecularly targeted therapies, specifically those directed at the BRAF/MEK/ERK signaling cascade (e.g., trametinib is an example of a MEK inhibitor) as well as for gemcitabine/nab-paclitaxel and FOLFIRINOX-related regimens (e.g., FOLFIRI or FOLFOX or 5-FU/nal-Irinotecan). In this example embodiment, it was observed that the PFS on therapies including a BRAF/MEK/ERK inhibitor was significantly longer in patients who were identified within the BRAF V600 Persona Type as, compared to patients in the BRAF "Other" Persona Type ($p<0.01$). Moreover, trends towards significance were observed when comparing the BRAF Fusion Persona Type to the BRAF "Other" Persona Type for BRAF/MEK/ERK inhibitors. However, the system also detected a trend for increased PFS on FOLFIRINOX-related therapies specifically in the BRAF Fusions Persona Type. The below example data is for illustrative purposes, and is not intended to be limiting in any manner.

Summary of PFS in weeks for each class of therapies and for each BRAF-mutant pancreatic cancer Persona Type:
FOLFIRINOX, Class 1 (V600) (mPFS=24, n=7)
FOLFIRINOX, Class 2 (Fusion) (mPFS=38, n=16)
FOLFIRINOX, Class 2 (non-V600) (mPFS=15.5, n=11)
FOLFIRINOX, Other (mPFS=20.7, n=12)
Gem/nab-P, Class 1 (V600) (mPFS=33, n=3)
Gem/nab-P, Class 2 (Fusion) (mPFS=12, n=12)
Gem/nab-P, Class 2 (non-V600) (mPFS=23, n=12)
Gem/nab-P, Other (mPFS=18, n=13)
BRAF/MEK/ERK inhibitor, Class 1 (V600) (mPFS=48, n=3)
BRAF/MEK/ERK inhibitor, Class 2 (Fusion) (mPFS=51.5, n=6)
BRAF/MEK/ERK inhibitor, Class 2 (non-V600) (mPFS=8, n=6)
BRAF/MEK/ERK inhibitor, Other (mPFS=7, n=3)

Accordingly, the traditional classification of 3 categories of BRAF alterations is distinct from, and falls short of, the persona typing approach discussed at length herein in three important ways. The first distinction indicator is that it was not immediately obvious why the persona typing method converged on these four persona types within the BRAF-mutant pancreatic cancer cohort based on the patient data. The second distinction indicator is that the outcome-driven persona typing approach itself was novel as implemented because the process of leveraging treatment-related outcomes for BRAF/MEK/ERK inhibitors was critically important to the creation of the two distinct sub-classification (i.e., BRAF non-V600 persona types and BRAF Fusions persona types) within the traditional "Class 2" categorization method for BRAF pathway alterations. Upon investigating differences in mPFS for standard therapies across the 4 BRAF-mutant pancreatic cancer persona types, a 5-fold difference (i.e., trending towards significance) in the mPFS for FOLFIRINOX-related therapies observed between the two "Class 2" subclasses was discovered.

Thus, the use of a persona typing approach revealed a potentially novel biomarker-treatment association via a semi-supervised classification approach using clinical and/or molecular data as well as clinical outcomes. Accordingly, it would be obvious to someone of ordinary skill in the art to recognize that the persona typing method, discussed herein, was responsible for discovering an emergent phenomenon. Moreover, in some embodiments, the persona typing approach may be extended in various ways to identify novel biomarker-treatment associations and re-evaluate existing biomarker-treatment assertions using supervised and semi-supervised approaches.

Finally, the third distinction indicator was that this method was applied in a cohort of BRAF-mutant pancreatic cancer. It is noted that BRAF mutations, generally, are relatively rare in pancreatic cancer (i.e., ~2-3% prevalence) and only recently has the scientific community made systematic efforts to functionally classify BRAF variants based on biological and structural properties of the mutations as well as how they functionally impact the BRAF protein and how specific drugs bind to the kinase domain, or other domains of the protein.

In the current illustrative embodiment, the system not only recapitulated the stratification of the established "Class 1", "Class 2", and "Class 3" categories of BRAF alterations, but also enabled the identification of two novel sub-classifications within "Class 2" BRAF alterations. As a result, any new patients with BRAF-mutant pancreatic cancer can be readily assigned to one of these four persona types which could potentially be clinically relevant for treatment selection. Additionally, the system found that outcomes for BRAF/MEK/ERK inhibitors were trending toward significant differences between the two persona types within the "Class 2" category (e.g., with BRAF Fusions demonstrating potentially longer mPFS than BRAF non-V600 mutation). However, mPFS on BRAF/MEK/ERK inhibitors is modestly higher for non-V600 compared to "Class 3 Other" alterations which is consistent with the rationale for the creation of "Class 3/Other" as a category.

The division of the traditional "Class 2" superset of BRAF pathway alterations may be in-part related to one or more distinct biomarker-treatment associations that were used to summarize BRAF Fusion and BRAF non-V600 (e.g., in the preprocessing workflow that is applied to the molecular data). In one embodiment, the preprocessing steps may have been driven by how experts perceived and manually classified the individual mutations (e.g., based on their knowledge of outcomes in other cancer types with similar mutations with similar structural/biological consequences). In another embodiment, a consensus-based approach may be used to determine the final interpretation of each patient's molecular alterations (e.g., BRAF mutation category) and the numerical values used to represent feasibility of BRAF/MEK/ERK inhibitors based on an expert opinion of the molecular findings and other patient data.

In a semi-supervised persona typing embodiment, the system may leverage traditional data science approaches that also serve as sanity checks, such as, for example: K-means clustering, random forest modeling, principal component analysis, Pearson's correlation analysis, Spearman's correlation analysis, and the like to find provisional explanatory variables when censored data is ignored.

As noted above, once the weights for various molecular data have been determined, an algorithm can be used to refine the weights based upon, for example, outcome data. In certain implementations, the outcome data can include values for overall survival, progression-free survival on a specific drug, and/or response rate to a specific drug.

The algorithm as described herein can include machine learning or other similar statistical-based modeling techniques. For example, the algorithm that is used may depend on an expected outcome of the algorithm. For example, a processing device can be configured to use a first process or algorithm to calculate refinements to a derived weight as described above based upon a first set of outcomes data while using a second or different process/algorithm to calculate refinements to a derived weight as described above based upon a second set of outcomes data. Different methods and algorithms may be used to calculate the refined weights in concert or substantially simultaneously. The output of each of the different methods and algorithms can then be compared and further analyzed to determine which output is highest rated. Alternatively, the output of each method and algorithm can be combined into a combinational metric.

In some implementations, a machine learning model as described in further detail below can be trained on a large population, for example, a population that can range from several thousand to tens of thousands of patient records comprising electrophysiology, demographic and medical history information. The machine learning tool can include, but is not limited to, penalized regression/classification techniques such as random forest and gradient boosting (e.g., implemented using R or any other statistical/mathematical programming language), Bayesian belief networks, and collaborative filters. Any other classification based machine learning tool can be used, including neural networks (as described in more detail below) and support vector machines. Because the machine learning tool may be computationally intensive, some or all of the processing for the machine learning tool may be performed on a server that is separate from the medical device.

An overview of how a random forest tool may be applied to a given dataset can illustrate how a classification tool may work in interpreting given input data. A random forest is a collection of decision trees. A decision tree is a flow chart-like structure in which each node represents a test on a metric and each branch represents the outcome of the test. The tree culminates in a classification label (e.g., a decision taken at the end after computing each of the metrics). Each tree in a random forest tool gets a "vote" in classifying a given set of metrics. There are two components of randomness involved in the building of a random forest. First, at the creation of each tree, a random subsample of the total data set is selected to grow the tree. Second, at each node of the tree, a "splitter variable" is selected and the underlying patients are separated into two classes. For example, patients in one class (e.g., positive response to a specific drug) can be separated from those in another class (e.g., negative response to a specific drug). The tree is grown with additional splitter variables until all terminal nodes (leaves) of the tree are purely one class or the other. The tree is "tested" against patient records that have been previously set aside. Each patient testing record traverses the tree, going down one branch or another depending on the metrics included in the record for each splitter variable. The patient testing record is assigned a predicted outcome based on where the record lands in the tree (a vote). The entire process may be repeated with new random divisions of the underlying dataset to produce additional trees and ultimately a "forest". In each case, different subsets of patients can be used to build the tree and test its performance In developing the results described in the below example implementation, a predetermined number of model variations are trained. For example, each model variation is labeled sequentially (e.g., for 100 runs, labeled from 1-100). In each run of the model, the software randomly samples a predetermined portion (e.g., an 80% portion) of the population as the training set and sets aside the remainder (e.g., 20%) as the validation set.

As noted above, the machine learning tool can train the model on a first portion of the underlying dataset, and validate the model on a second portion of the dataset or on another separate dataset. When evaluating the performance of each model, the performance of the underlying decisions within the decision trees in the random forest can be evaluated based on specificity and sensitivity parameters. For example, the sensitivity parameter can be based on a measure of the model's ability to correctly predict whether a patient is at risk of reacting negatively to a drug treatment. For example, the sensitivity parameter may be based on a proportion of patients that the model correctly predicts will react negatively to the treatment.

The specificity parameter can be based on the proportion of patients who are to be treated with a specific drug, and who are predicted by the relevant model to react positive to the drug treatment. It may be advantageous to optimally balance individual performance variables such as sensitivity and specificity at a high level. For example, by setting the specificity at a relatively high value (e.g., 95%), the underlying thresholds within the classifier model may be adjusted to minimize false positives. After the specificity is defined, the measure of sensitivity can be treated as a type of performance measure (e.g., generally in the range of 15-35% for a given model); however, smaller or larger values of sensitivity are also possible.

A validation protocol, for example, as described below, can be employed to validate the predictive performance of trained models. In an implementation, the validation phase can be used to ascertain appropriate threshold scores for classifying future patients (e.g., where an outcome is currently unknown and a prediction of the outcome is desired) and to determine the predictive performance of each classifier model generated by the machine learning tool. For validating the various models and associated threshold scores, a second group of individuals (e.g., a validation population (or cohort)) can be used.

For example, the validation population can be a new validation population. The outcome for the patients in the validation cohort is eventually learned as these patients progress through treatment. In an embodiment, the patients in the validation population can be different from the group of training and test patients described above for training the model. For example, a validation population of patients and their associated metrics (e.g., validation metrics) can be independent from a training population of patients and associated metrics (e.g., training metrics). In some implementations, there may be an overlap between the validation metrics and the training metrics.

In some implementations, the validation population can be updated by at least one of 1) adjusting one or more of the metrics in the validation metrics, and 2) expanding the validation metrics based on appending an additional one or more subjects to a population of subjects that make up the validation population. The thresholds for classifying future patients can be refined based on the updated validation metrics. For example, metrics of a patient that is currently being treated or monitored or has otherwise not progressed through the treatment can be used to adjust the one or more metrics in the validation metrics, or the patient's metrics can be added to the validation population as metrics from a new subject. The validation metrics can be adjusted as new metrics for the patient are determined during the monitoring or treatment of the patient. In some examples, as a monitored patient progresses through treatment, the patient's metrics can be added to the validation population and/or used to adjust the metrics in the validation metrics after the patient has progressed through the treatment.

In some implementations, the training population can be updated by at least one of 1) adjusting one or more of the metrics in the training metrics, and 2) expanding the training metrics based on appending one or more additional subjects to the first plurality of subjects. The machine learning classifier models can be retrained based on the updated training metrics. For example, as additional patient metrics are determined from current patients and/or metrics from new patients are determined, the machine learning model can be retrained (e.g., on the increased number of metrics or on new, different metrics to provide updated classifier models). The training population can be updated as new metrics for current patients and/or metrics for new patients are determined or after patients have progressed through treatment.

Figure 6:
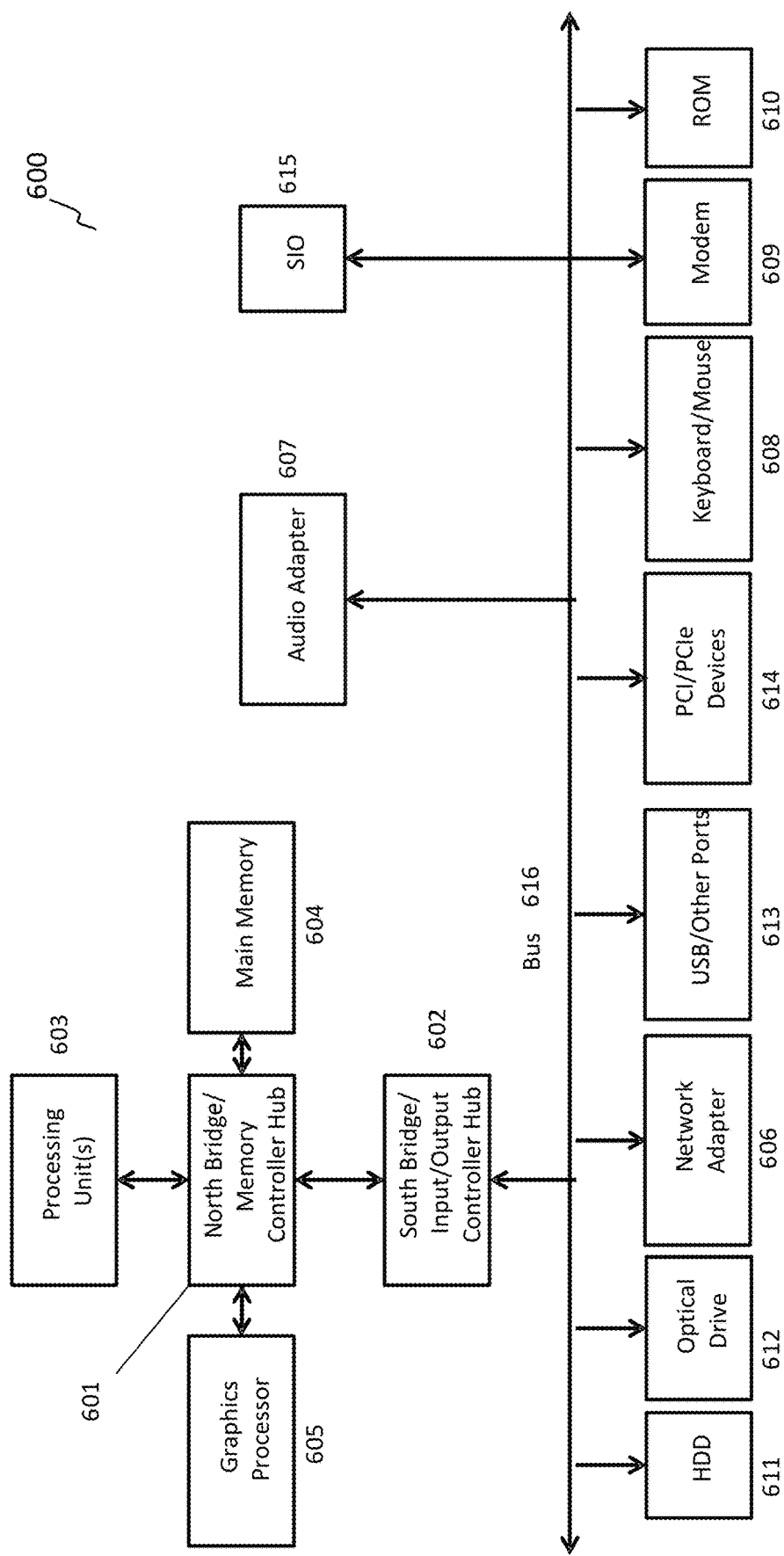
FIG. 6 depicts an illustrative computer system in accordance with an embodiment.

FIG. 6 is a block diagram of an illustrative data processing system 600 in which aspects of the illustrative embodiments are implemented. Data processing system 600 is an example of a computer, such as a server or client, in which computer usable code or instructions implementing the process for illustrative embodiments of the present invention are located. In some embodiments, the data processing system 600 may be a server computing device.

In the depicted example, data processing system 600 can employ a hub architecture including a north bridge and memory controller hub (NB/MCH) 601 and south bridge and input/output (I/O) controller hub (SB/ICH) 602. Processing unit 603, main memory 604, and graphics processor 605 can be connected to the NB/MCH 601. Graphics processor 605 can be connected to the NB/MCH 601 through, for example, an accelerated graphics port (AGP).

In the depicted example, a network adapter 606 connects to the SB/ICH 602. An audio adapter 607, keyboard and mouse adapter 608, modem 609, read only memory (ROM) 610, hard disk drive (HDD) 611, optical drive (e.g., CD or DVD) 612, universal serial bus (USB) ports and other communication ports 613, and PCI/PCIe devices 614 may connect to the SB/ICH 602 through bus system 616. PCI/PCIe devices 614 may include Ethernet adapters, add-in cards, and PC cards for notebook computers. ROM 610 may be, for example, a flash basic input/output system (BIOS). The HDD 611 and optical drive 612 can use an integrated drive electronics (IDE) or serial advanced technology attachment (SATA) interface. A super I/O (SIO) device 615 can be connected to the SB/ICH 602.

An operating system can run on processing unit 603. The operating system can coordinate and provide control of various components within the data processing system 600. As a client, the operating system can be a commercially available operating system. An object-oriented programming system, such as the Java™ programming system, may run in conjunction with the operating system and provide calls to the operating system from the object-oriented programs or applications executing on the data processing system 600. As a server, the data processing system 600 can be an IBM® eServer™ System p® running the Advanced Interactive Executive operating system or the Linux operating system. The data processing system 600 can be a symmetric multiprocessor (SMP) system that can include a plurality of processors in the processing unit 603. Alternatively, a single processor system may be employed.

Instructions for the operating system, the object-oriented programming system, and applications or programs are located on storage devices, such as the HDD 611, and are loaded into the main memory 604 for execution by the processing unit 603. The processes for embodiments described herein can be performed by the processing unit 603 using computer usable program code, which can be located in a memory such as, for example, main memory 604, ROM 610, or in one or more peripheral devices.

A bus system 616 can be comprised of one or more busses. The bus system 616 can be implemented using any type of communication fabric or architecture that can provide for a transfer of data between different components or devices attached to the fabric or architecture. A communication unit such as the modem 609 or the network adapter 606 can include one or more devices that can be used to transmit and receive data.

Those of ordinary skill in the art will appreciate that the hardware depicted in FIG. 6 may vary depending on the implementation. Other internal hardware or peripheral devices, such as flash memory, equivalent non-volatile memory, or optical disk drives may be used in addition to or in place of the hardware depicted. Moreover, the data processing system 600 can take the form of any of a number of different data processing systems, including but not limited to, client computing devices, server computing devices, tablet computers, laptop computers, telephone or other communication devices, personal digital assistants, and the like. Essentially, data processing system 600 can be any known or later developed data processing system without architectural limitation.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by ⅒ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of improved modeling and outcome-driven persona-typing to generate targeted oncology patient treatment plans, the method implemented by a server computing device and comprising:
   generating a structured database comprising a plurality of data fields from a first data set obtained for each of a plurality of first patients, wherein one or more of the data fields comprise multivariate quantitative data and the first data set comprises first patient specific data including treatment data and a clinical outcome for an associated one of the first patients;
   analyzing the structured database based on at least one selective pressure filter to generate a machine learning model, wherein the at least one selective pressure filter comprises the clinical outcome, one or more of the data fields are weighted in the machine learning model based on a level of which each of the one or more of the data fields discriminates between a plurality of patient groups of the first patients, and each of the patient groups corresponds to one of a plurality of personas;
   receiving a second data set for a second patient, wherein the second data set comprises second patient-specific data;
   applying the machine learning model to the second data set to classify the second patient as associated with one of the personas, wherein the machine learning model is configured to classify second patient-specific data of the second data set into one of the patient groups corresponding to the one of the personas; and
   outputting an oncology patient treatment plan for the second patient, wherein the oncology patient treatment plan is associated with the one of the personas and is determined from at least a portion of the treatment data associated with one or more of the first patients of the one of the patient groups.

2. The method of claim 1, wherein the oncology patient treatment plan comprises at least one of: a listing of one or more potential treatment options; a listing of eligibility for one or more clinical trials; a listing of drug cost-effectiveness; a healthcare economics report; an availability of one or more drugs; a list of one or more suggested additional tests; one or more risk assessment scores; or one or more benefit scores.

3. The method of claim 1, wherein the second data set comprises treatment information associated with a previous treatment plan for the second patient, the second patient having a previously determined persona type.

4. The method of claim 3, further comprising:
   identifying, based on the treatment information, at least one characteristic value of the previously determined persona type that exceeds a threshold; and
   modifying, based on the treatment information, the at least one characteristic value.

5. The method of claim 4, further comprising creating a new persona type, wherein the new persona type is created based on an existing one of the plurality of personas and the modified at least one characteristic value.

6. The method of claim 1, wherein the patient-specific data comprises at least one of clinical data or molecular data.

7. The method of claim 6, wherein the clinical data comprises at least one of medical records, clinical attributes, prognostic factors, treatment history, surgical history, quality of life, or quantity of life.

8. The method of claim 6, wherein the molecular data comprises at least one of genomic alterations, protein intensity, protein staining, phosphoprotein expression, transcriptomic profiling, metabolomics fluctuations, microbiome diversity, or multi-omic derivations.

9. A server computing device, comprising:
   a processor; and
   memory storing instructions that, when executed by the processor, cause the server computing device to:
      generate a structured database comprising a plurality of data fields from a first data set obtained for each of a plurality of first patients, wherein one or more of the data fields comprise multivariate quantitative data and the first data set comprises first patient specific data including treatment data and a clinical outcome for an associated one of the first patients;
      analyze the structured database based on at least one selective pressure filter to generate a machine learning model, wherein the at least one selective pressure filter comprises the clinical outcome, one or more of the data fields are weighted in the machine learning model based on a level of which each of the one or more of the data fields discriminates between a plurality of patient groups of the first patients, and each of the patient groups corresponds to one of a plurality of personas;
      receive a second data set for a second patient, wherein the second data set comprises second patient-specific data;
      apply the machine learning model to the second data set to classify the second patient as associated with one of the personas, wherein the machine learning model is configured to classify second patient-specific data of the second data set into one of the patient groups corresponding to the one of the personas; and
      output an oncology patient treatment plan for the second patient, wherein the oncology patient treatment plan is associated with the one of the personas and is determined from at least a portion of the treatment data associated with one or more of the first patients of the one of the patient groups.

10. The server computing device of claim 9, wherein the oncology patient treatment plan comprises at least one of: a listing of one or more potential treatment options; a listing of eligibility for one or more clinical trials; a listing of drug cost-effectiveness; a healthcare economics report; an availability of one or more drugs; a list of one or more suggested additional tests; one or more risk assessment scores; or one or more benefit scores.

11. The server computing device of claim 9, wherein the second data set comprises treatment information associated with a previous treatment plan for the second patient, the second patient having a previously determined persona type.

12. The server computing device of claim 11, wherein the instructions, when executed by the processor are further configured to cause the server computing device to:
   identify, based on the treatment information, at least one characteristic value of the previously determined persona type that exceeds a threshold; and
   modify, based on the treatment information, the at least one characteristic value.

13. The server computing device of claim 12, wherein the instructions, when executed by the processor are further configured to cause the server computing device to create create a new persona type, wherein the new persona type is created based on an existing one of the plurality of personas and the modified at least one characteristic value.

14. The server computing device of claim 9, wherein the patient-specific data further comprises at least one of clinical data or molecular data.

15. The server computing device of claim 14, wherein the clinical data comprises at least one of medical records, clinical attributes, prognostic factors, treatment history, surgical history, quality of life, or quantity of life.

16. The server computing device of claim 9, wherein the molecular data further comprises at least one of genomic alterations, protein staining, phosphoprotein expression, transcriptomic profiling, metabolomics fluctuations, protein intensity, microbiome diversity; or multi-omic derivations.

17. A non-transitory computer readable medium having stored thereon instructions for improved modeling and outcome-driven persona-typing to generate targeted oncology patient treatment plans comprising executable code that, when executed by a processor, causes the processor to:
   generate a structured database comprising a plurality of data fields from a first data set obtained for each of a plurality of first patients, wherein one or more of the data fields comprise multivariate quantitative data and the first data set comprises first patient specific data including treatment data and a clinical outcome for an associated one of the first patients;
   analyze the structured database based on at least one selective pressure filter to generate a machine learning model, wherein the at least one selective pressure filter comprises the clinical outcome, one or more of the data fields are weighted in the machine learning model based on a level of which each of the one or more of the data fields discriminates between a plurality of patient groups of the first patients, and each of the patient groups corresponds to one of a plurality of personas;
   receive a second data set for a second patient, wherein the second data set comprises second patient-specific data;
   apply the machine learning model to the second data set to classify the second patient as associated with one of the personas, wherein the machine learning model is configured to classify second patient-specific data of the second data set into one of the patient groups corresponding to the one of the personas; and
   output an oncology patient treatment plan for the second patient, wherein the oncology patient treatment plan is associated with the one of the personas and is determined from at least a portion of the treatment data associated with one or more of the first patients of the one of the patient groups.

\* \* \* \* \*